US009012020B2

(12) United States Patent
Wittenbecher et al.

(10) Patent No.: US 9,012,020 B2
(45) Date of Patent: Apr. 21, 2015

(54) BLENDS COMPRISING EPOXY RESINS AND MIXTURES OF AMINES WITH GUANIDINE DERIVATIVES

(71) Applicant: BASF SE, Ludwigshafen (DE)

(72) Inventors: Lars Wittenbecher, Duesseldorf (DE); Michael Henningsen, Frankenthal (DE); Gregor Daun, Neckargemuend (DE); Dieter Flick, Boehl-Iggelheim (DE); Joerg-Peter Geisler, Bingen (DE); Juergen Schillgalies, Moers (DE); Erhard Jacobi, Huenstetten (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/141,058

(22) Filed: Dec. 26, 2013

(65) Prior Publication Data

US 2014/0107255 A1 Apr. 17, 2014

Related U.S. Application Data

(63) Continuation of application No. 13/055,174, filed as application No. PCT/EP2009/059238 on Jul. 17, 2009, now Pat. No. 8,741,426.

(30) Foreign Application Priority Data

Jul. 22, 2008 (EP) .................................... 08160857
Jul. 8, 2009 (EP) .................. PCT/EP2009/058699

(51) Int. Cl.
| *B32B 27/04* | (2006.01) |
| *B32B 27/26* | (2006.01) |
| *B32B 27/38* | (2006.01) |
| *C08G 59/50* | (2006.01) |
| *C08G 59/56* | (2006.01) |
| *C08L 63/00* | (2006.01) |
| *C08G 59/02* | (2006.01) |
| *C07C 279/04* | (2006.01) |
| *C07C 279/16* | (2006.01) |

(52) U.S. Cl.
CPC ............. *C08G 59/02* (2013.01); *C07C 279/04* (2013.01); *C07C 279/16* (2013.01); *C08L 63/00* (2013.01)

(58) Field of Classification Search
USPC ............... 264/239, 241, 257; 428/297.4, 413; 523/400, 428
See application file for complete search history.

(56) References Cited

U.S. PATENT DOCUMENTS

| 3,308,094 | A | 3/1967 | Sherr |
| 4,269,879 | A | 5/1981 | Davis |
| 6,399,199 | B1 | 6/2002 | Fujino et al. |
| 6,491,845 | B1 | 12/2002 | Schile |
| 6,935,573 | B2 | 8/2005 | Kobayashi et al. |
| 2002/0082379 | A1 | 6/2002 | Schile |
| 2003/0018131 | A1 | 1/2003 | Davis et al. |
| 2003/0108700 | A1 | 6/2003 | Krech et al. |
| 2004/0059035 | A1 | 3/2004 | Krech et al. |
| 2005/0143496 | A1 | 6/2005 | Mueller |
| 2006/0135706 | A1 | 6/2006 | Davis et al. |
| 2011/0130524 | A1* | 6/2011 | Wittenbecher et al. ........ 525/523 |
| 2011/0180970 | A1* | 7/2011 | Wittenbecher et al. .. 264/331.12 |
| 2011/0190419 | A1* | 8/2011 | Wittenbecher et al. ........ 523/400 |

FOREIGN PATENT DOCUMENTS

| CZ | 242020 | 8/1985 |
| DE | 10 2005 018 671 | 10/2006 |
| DE | 10 2006 056 311 | 6/2008 |
| EP | 0 659 833 | 6/1995 |
| EP | 1 358 997 | 11/2003 |
| EP | 1 715 003 | 10/2006 |
| JP | 61-83218 | 4/1986 |
| JP | 61-207425 | 9/1986 |
| JP | 63017938 A * | 1/1988 ................. C08J 5/24 |
| JP | 2002 187936 | 7/2002 |
| JP | 2002 240205 | 8/2002 |
| JP | 2005 067209 | 3/2005 |
| WO | 02 42349 | 5/2002 |
| WO | 02 070623 | 9/2002 |
| WO | 03 045801 | 6/2003 |
| WO | 2004 020506 | 3/2004 |
| WO | 03 002667 | 1/2007 |
| WO | 2007/107288 | 9/2007 |

OTHER PUBLICATIONS

Translation of JP 63017938 A, provided by USPTO translations (no date).*
International Search Report issued Sep. 10, 2009 in PCT/EP09/059238 filed Jul. 17, 2009.
Bruce L. Burton et al., "Epoxy formulations using Jeffamine® Polyethermaines"; Huntsman Corp., Apr. 27, 2005 (103 pages).
Bruce L. Burton, "Amine Curing of Epoxy Resins: Options and Key Formulation Considerations", www.picmag.com Huntsman Corp., Jun. 2006 (pp. 68-77).
Allan E. Sherr et al., "Base Catalysts for the Cure of Epoxy Resins", Journal of Applied Polymer Science, vol. 9, 1965 (pp. 2707-2714).
E-Composites, Inc., "Growth Opportunities in Wind Energy Market 2006-2011: Materials, Market and Technologies", 2006 (6 pages).
Bodo Muller et al., "Coatings Formulation", Coatings Compendia, 2006 (pp. 110-121, 257).
Henry Lee et al., "Handbook of Epoxy Resins", McGraw-Hill, Inc. 1967 (4 pages).

(Continued)

*Primary Examiner* — Michael J Feely
(74) *Attorney, Agent, or Firm* — Oblon, McClelland, Maier & Neustadt, L.L.P.

(57) ABSTRACT

The present invention provides a blend comprising one or more epoxy resins and a mixture which comprises 0.3 to 0.9 amine equivalent, per equivalent of epoxide of the epoxy resin used, of a hardener component a) and as hardener component b) a compound of the formula I, a process for preparing this blend, the use of the blend of the invention for producing cured epoxy resin, and an epoxy resin cured with the blend of the invention.

14 Claims, 2 Drawing Sheets

(56) References Cited

OTHER PUBLICATIONS

S.L. Simon et al., "Reaction Kinetics and TTT Cure Diagrams for Off-Stoichiometric Ratios of a High-Tg Epoxy/Amine System", Journal of Applied Polymer Science, vol. 46, May 12, 1992 (pp. 1245-1270).
Derk Visser, "The Annotated European Patent Convention", 2010 (p. 105).
"The Jeffamine® Polyetheramines", product specification of Huntsman available from www.huntsman.com, 2007 (6 pages).
Goodman, Sidney, "Handbook of Thermoset Plastics", Noyes Publications, 1998 (1 page).
Eberl Ulrich et al., "Innovative Minds—A Look Inside Siemens' Idea Machine" Publicis KommunikationsAgentur GmbH 2007 (1 page).
Rebecca Dolbey, "RAPRA Review Reports—Expert Overviews covering the Science and Technology of Rubber and Plastics", Rapra Technology Limited, 1997 (1 page).
Hexion Specialty Chemicals, "Formulating High Performance Waterborne Epoxy Coatings", 2005 (pp. 1-28).
G.R. Palmese et al., "Effect of Epoxy—Amine Stoichiometry on Cured Resin Material Properties", Journal of Applied Polymer Science, vol. 46 1992 (pp. 1863-1873).
Clara D. Craver et al., Applied Polymer Science $21^{st}$ Century, Dec. 19, 2000 (6 pages).
English Translation of EP Opposition received in EP 2 307 359 B1 dated Sep. 20, 2012.
Notice of Opposition filed in corresponding EP Application No. 20090780778, (2012).
Becker, Gerhard W., et al.; "Kunststoff Handbuch" [Plastics Handbook]; $2^{nd}$ fully revised edition, 1988; ISBN 3-448-14418-8; Duroplaste [Thermosets] (English translation).
Stoye, Dieter et al.; "Lackharze"[Resins for coatings]; Chemistry Properties Application; 1996; ISBN 3-446-17475-3 (English translation).

* cited by examiner

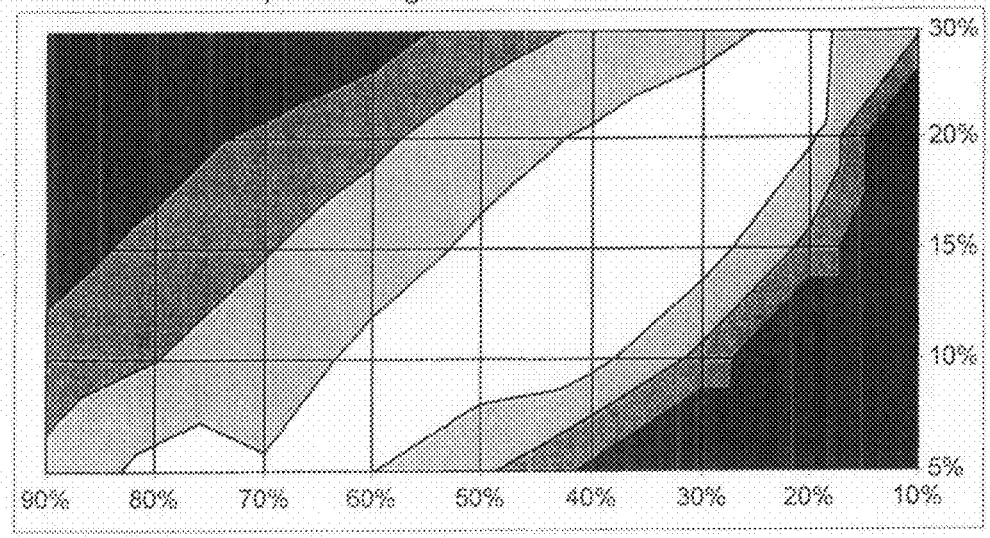
Glass transition temperature figure 1
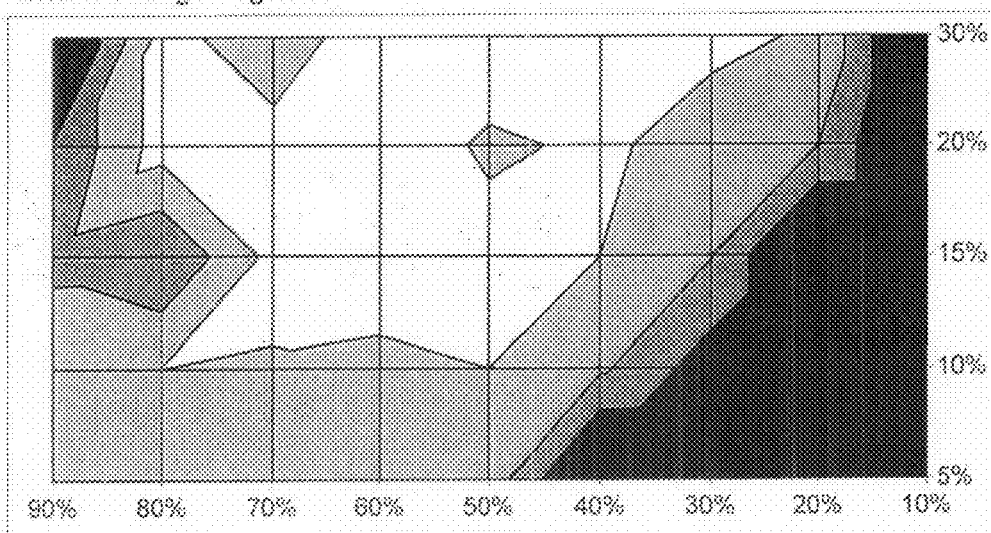
Flexural strength figure 2

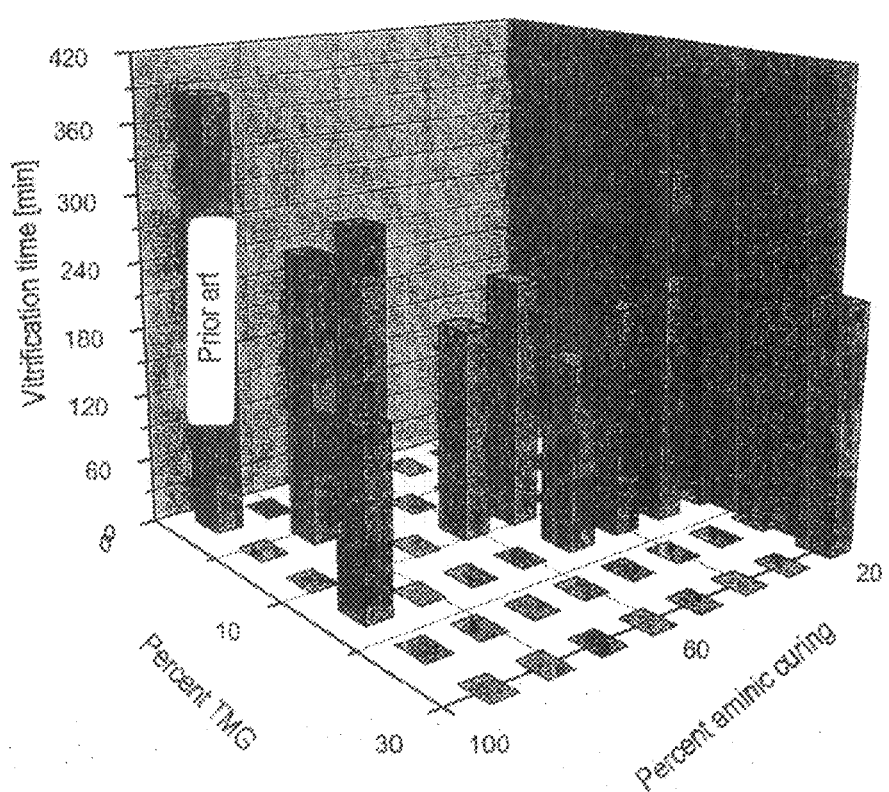

BLENDS COMPRISING EPOXY RESINS AND MIXTURES OF AMINES WITH GUANIDINE DERIVATIVES

CROSS REFERENCE TO RELATED APPLICATIONS

The present application is a Continuation of U.S. Ser. No. 13/055,174 (now U.S. Pat. No. 8,741,426), filed Apr. 15, 2011, which was a 371 of international PCT application PCT/EP2009/059238, filed Jul. 17, 2009. The present application further claims priority to European application EP 08150857.2, filed Jul. 22, 2008 in the European Patent Office, and PCT/EP2009/058699, filed Jul. 8, 2009.

The present invention provides a blend comprising one or more epoxy resins and a mixture which comprises 0.3 to 0.9 amine equivalent, per equivalent of epoxide of the epoxy resin used, of a hardener component a) and as hardener component b) a compound of the formula I, a process for preparing this blend, the use of the blend of the invention for producing cured epoxy resin, and an epoxy resin cured with the blend of the invention.

The amine curing of epoxy resins is utilized in a very wide variety of segments. For instance, the amine curing of epoxy resins is employed in the context of adhesives, for the curing of casting resins in special molds, and also for the sealing of surfaces and components to be protected from environmental effects.

One specific, large field of application of the amine curing of epoxy resins is the production of fiber-reinforced plastics. Fiber-reinforced plastics are used as materials of construction for motor vehicles, aircraft, ships and boats, for sports articles and for rotor blades of wind turbines.

The production of large components imposes particular requirements on the hardener or hardener mixture, since during the processing life the viscosity must not rise so sharply that either the fibers are not adequately wetted or else the mold is not completely filled before the epoxy resin becomes no longer processable.

At the same time there ought not to be any adverse effect on the cycle time (processing and curing). Consequently there is a great need for mixtures which are capable of precisely controlling and setting the curing of the epoxy resin in any systems.

H. Klein, in "Huntsman Amine Overview", Huntsman, Jun. 19, 2007, Beijing Epoxy Conference, describes how primary and secondary diamines and polyetheramines can generally be used to cure epoxy resins. A blend in which the hardener component a) is used in the range from 0.3 to 0.9 amine equivalent, per equivalent of epoxide of the epoxy resin used, and in which the hardener component b) is a compound of the formula I, is not described, however.

B. Burton, D. Alexander, H. Klein, A. Garibay Vasquez, and C. Henkee, in the product brochure "Epoxy formulations using Jeffamine Polyetheramines", Huntsman, Apr. 21, 2005, describe the stoichiometric use of polyetheramines, or a mixture of polyetheramines and other diamines such as isophoronediamine (IPDA), as a particular form of the amine curing of epoxy resins. The systems in question are two-component systems in which the amine or amine mixture is added to the epoxy resin immediately prior to curing, in amounts which comprise exactly the same number of active amine functions in the amine mixture as there are active epoxide functions in the epoxides.

In hardener formulations comprising polyetheramines and IPDA, the effect of the latter is on the one hand a higher cure rate and on the other hand the observation of higher glass transition temperatures in the cured resins, leading to a higher temperature stability on the part of the cured products—as required for certain applications such as the production of rotor blades, for example—than is the case with curing at comparable temperature using pure polyetheramine.

As compared with the curing of epoxy resins by polyetheramines, however, the addition of IPDA entails not only a higher glass transition temperature on the part of the cured resins but also more rapid curing, which is accompanied by a more rapid increase in viscosity. As a result, the time within which the blend of epoxy resin and hardener/hardener mixture can still be processed is reduced. A disadvantage with hardener mixture systems of this kind, therefore, is that the production of large components, such as rotor blades, is possibly unsuccessful, because the infusion process remains incomplete on account of the development of viscosity.

The rate of the stoichiometric curing of epoxy resins with amines can also be increased by adding tertiary amines to the blend, which function as accelerants. This addition as well leads usually to a more rapid increase in viscosity at room temperature and to shorter pot lives. The pot life or else gelling time is a variable which is commonly utilized to compare the reactivity of different resin/hardener combinations and/or resin/hardener mixture combinations. The measurement of pot life/gelling time (To) is described according to the specification of ASTM D 2471-99 and is a method of characterizing the reactivity of laminating systems by means of a temperature measurement. Depending on application, deviations from the parameters described therein (amount, test conditions, and measurement method) have become established, resulting in a pot life A (ToA) and a pot life B (ToB).

The pot life A (ToA) is determined as follows:

100 g of the blend, comprising epoxy resin and hardener or hardening mixture, are introduced into a container (typically a cardboard carton). A temperature sensor is immersed into this blend, and measures and stores the temperature at defined time intervals. As soon as this blend has solidified, measurement is ended and the time taken to attain the maximum temperature is determined. Where the reactivity of a blend is too low, this measurement is carried out at elevated temperature. As well as the pot life, it is always necessary to report the testing temperature as well.

Pot life B (ToB) is determined as follows:

5 g of the blend comprising epoxy resin and hardener/hardener mixture are introduced in a 5 ml penicillin bottle at a given testing temperature (not adiabatically). A circular die (Ø 11.8 mm) moves up and down (1 mm/sec) in the blend. When a corresponding resistance (about 5 kPa) is reached, the stopwatch is shut off.

Examples of above-described accelerants specified in U.S. Pat. No. 4,948,700, column 10, are triethanolamine, benzyldimethylamine, 2,4,6-tris(dimethylaminomethyl)phenol, and tetramethylguanidine. The fundamental suitability of tetra- and penta-alkylguanidines as hardeners of epoxy resin mixtures is described in U.S. Pat. No. 3,308,094. The use of tetramethylguanidine as a tertiary amine with a very low catalytic activity is also mentioned in U.S. Pat. No. 6,743,375 in column 19. U.S. Pat. No. 6,743,375, however, teaches the skilled worker that tetramethylguanidine is a comparatively slow accelerant. A blend in which the hardener component a) is used in the range from 0.3 to 0.9 amine equivalent per equivalent of epoxide of the epoxy resin used and the hardener component b) is a compound of the formula I is not described, however.

Among the technologies employing the curing of epoxides with amines are infusion technologies. In these cases, diepoxy and polyepoxy resins are mixed with amines and polyetheramines immediately prior to the infusion procedure, to form the blend, the blend is drawn into the respective mold under suction, at temperatures of 20° C.-50° C., and is subsequently reacted at molding temperatures of 55° C.-90° C., and the blend is cured as a result. The rate of the overall process is dependent on the duration of the infusion step itself and on the duration of curing. The lower the viscosity of the blend, the quicker the infusion procedure may take place. Reducing the viscosity of a given blend can be accomplished by raising the temperature in the course of the infusion procedure, thereby in principle making it quicker. Raising the temperature during the infusion procedure for the purpose of reducing the viscosity makes sense, however, only with amines of low reactivity, such as polyetheramines, for example. The disadvantage of the sole use of amines of low reactivity, such as polyetheramines, for example, is the slow reaction of this component with the epoxy resin, as a result of which the curing procedure is slow. The duration of curing can be shortened through the use of particularly reactive amines such as IPDA, for example. Where these reactive amines are present, however, infusion must take place at low temperatures, since the viscosity of a mixture of polyetheramine and IPDA at temperatures>40° C. rises so rapidly that it is no longer possible to ensure complete impregnation of the fiber mats.

In the use of infusion technologies such as vacuum assisted resin transfer molding (VARTM) technology for the production of large components, a long pot life on the part of the blend comprising epoxy resins and amines, in the region of several hours at room temperature, may be necessary in order to ensure a trouble-free infusion procedure. This long pot life can be achieved through the use of polyetheramines of low reactivity, as are described in WO-A 2004/020506, pages 14-17. In the state of the art for infusion technology, the exclusive use of active hardeners such as IPDA is unknown for large components. The disadvantage of the use exclusively of polyetheramines of low reactivity in infusion technology lies in the extremely long cure times at elevated temperature, which prevent productivity increase and at the same time necessitate increased employment of energy.

Improvement in the infusion process with blends comprising epoxy resins and amines occurs when the viscosity of the blend during the infusion procedure is low, or when, as a result of a relatively long pot life on the part of the improved blend, the infusion procedure is able to take place at higher temperatures, and hence at a lower viscosity, than is the case for the existing blends of epoxy resins, polyetheramines, and IPDA. The object of an improved process for producing such moldings would be that of exhibiting a comparable or higher cure rate relative to the prior art at temperatures of, for example, 60° C. or more.

Such processes would specifically be very suitable for the manufacture of large components, since, with a comparable or shorter cure rate, the processing time at room temperature would be prolonged, or processing would be possible at higher temperatures, without premature curing of the blend, and hence complete and uniform curing would be enabled.

It is an object of the present invention, therefore, to provide a blend which allows the cure rate of the blend to be raised without at the same time increasing the viscosity of the blend during processing in such a way that complete filling of the mold and, if appropriate, uniform impregnation of existing fiber material is no longer possible.

This object is achieved by means of a blend comprising
α) one or more epoxy resins and
β) a mixture comprising
1) 0.3 to 0.9 amine equivalent, per equivalent of epoxide of component α) used, of a hardener component a) and
2) a hardener component b),
wherein the hardener component a) comprises one or more amines having a functionality≥2, and at least one amine, when mixed stoichiometrically with the epoxy resin in the 100 g batch, leads at room temperature to a cure time of less than 24 h, and the hardener component b) comprises at least one compound of the formula I

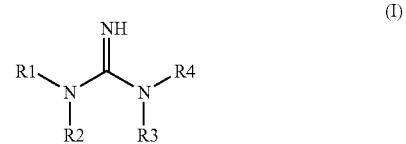

where R1 to R3, R5 and R6 each independently are an organic radical having 1 to 20 C atoms and hydrogen, and R4 is selected from the group of an organic radical having 1 to 20 C atoms and a group —C(NH)NR5R6.

Advantageous is the blend of the invention wherein the hardener component a) is selected from the group of amines having a functionality≥2.

Advantageous is the blend of the invention wherein the hardener component a) comprises at least two hardener components a1) and a2), the hardener component a1) being at least one polyetheramine having a functionality≥2 and the hardener component a2) being at least one further amine having a functionality≥2.

Advantageous is the blend of the invention wherein the hardener component a1) is selected from the group of 3,6-dioxa-1,8-octanediamine, 4,7,10-trioxa-1,13-tridecanediamine, 4,7-dioxa-1,10-decanediamine, 4,9-dioxa-1,12-dodecanediamine, polyetheramine based on triethylene glycol with an average molar mass of 148, difunctional, primary polyetheramine prepared by aminating an ethylene glycol grafted with propylene oxide, with an average molar mass of 176, difunctional, primary polyetheramine based on propylene oxide with an average molar mass of 4000, difunctional, primary polyetheramine prepared by aminating a polyethylene glycol grafted with propylene oxide, with an average molar mass of 2003, aliphatic polyetheramine based on polyethylene glycol grafted with propylene oxide, with an average molar mass of 900, aliphatic polyetheramine based on polyethylene glycol grafted with propylene oxide, with an average molar mass of 600, difunctional, primary polyetheramine prepared by aminating a diethylene glycol grafted with propylene oxide, with an average molar mass of 220, aliphatic polyetheramine based on a copolymer of poly(tetramethylene ether glycol) and polypropylene glycol with an average molar mass of 1000, aliphatic polyetheramine based on a copolymer of poly(tetramethylene ether glycol) and polypropylene glycol with an average molar mass of 1900, aliphatic polyetheramine based on a copolymer of poly(tetramethylene ether glycol) and polypropylene glycol with an average molar mass of 1400, polyethertriamine based on an at least trihydric alcohol grafted with butylene oxide, with an average molar mass of 400, aliphatic polyetheramine prepared by aminating alcohols grafted with butylene oxide, with an average molar mass of 219, polyetheramine based on pentaerythritol and propylene oxide with an average molar mass of 600, difunctional, primary polyetheramine based on polypropylene glycol with an average molar mass of 2000, difunctional, primary polyetheramine based on polypropylene glycol with an average molar mass of 230, difunctional, primary polyetheramine based on polypropylene glycol with an average molar mass of 400, trifunctional, primary polyetheramine prepared by reacting propylene oxide with trimethylolpropane, followed by amination of the terminal OH groups, with an average molar mass of 403, trifunctional, primary polyetheramine prepared by reacting propylene oxide with glycerol, followed by amination of the terminal OH groups, with an average molar mass of 5000, and a polyetheramine having an average molar mass of 400, prepared by aminating polyTHF which has an average molar mass of 250, and the hardener component a2) is selected from the group of 1,12-diaminododecane, 1,10-diaminodecane, 1,2-diaminocyclohexane, 1,2-propanediamine, 1,3-bis(aminomethyl)cyclohexane, 1,3-propanediamine, 1-methyl-2,4-diaminocyclohexane, 2,2'-oxybis(ethylamine), 3,3'-dimethyl-4,4'-diaminodicyclohexylmethane, 4,4'-methylenedianiline, 4-ethyl-4-methylamino-1-octylamine, diethylenetriamine, ethylenediamine, hexamethylenediamine, isophoronediamine, menthenediamine, xylylenediamine, N-aminoethylpiperazine, neopentanediamine, norbornanediamine, octamethylenediamine, piperazine, 4,8-diaminotricyclo[5.2.1.0]decane, tolylenediamine, triethylenetetramine, and trimethylhexamethylenediamine.

Advantageous is the blend of the invention wherein the radicals R1 to R3, R5, and R6 of the compounds of the formula I are each independently selected from the group of hydrogen, methyl, ethyl, n-propyl, isopropyl, n-butyl, sec-butyl, phenyl, and o-tolyl, and R4 is selected from the group of methyl, ethyl, n-propyl, isopropyl, n-butyl, sec-butyl, phenyl, o-tolyl, and a group —C(NH)NR5R6-.

Advantageous is the blend of the invention wherein the fraction of hardener component b), based on the weight fraction of the mixture, is 5% to 55% by weight.

Advantageous is the blend of the invention wherein the mixture comprises as hardener component a1) a polyetheramine having a functionality of z 2, selected from the group of difunctional, primary polyetheramine based on polypropylene glycol, with an average molar mass of 230, difunctional, primary polyetheramine based on polypropylene glycol, with an average molar mass of 400, aliphatic, difunctional, primary polyetheramine based on polypropylene glycol, with an average molar mass of 2000, difunctional, primary polyetheramine prepared by aminating a diethylene glycol grafted with propylene oxide, with an average molar mass of 220, trifunctional, primary polyetheramine prepared by reacting propylene oxide with trimethylolpropane, followed by amination of the terminal OH groups, with an average molar mass of 403, aliphatic polyetheramine based on polyethylene glycol grafted with propylene oxide, with an average molar mass of 900, aliphatic polyetheramine based on a copolymer of poly(tetramethylene ether glycol) and polypropylene glycol, with an average molar mass of 1000, aliphatic polyetheramine based on a copolymer of poly (tetramethylene ether glycol) and polypropylene glycol, with an average molar mass of 1900, aliphatic polyetheramine based on a copolymer of poly(tetramethylene ether glycol) and polypropylene glycol, with an average molar mass of 1400, polyethertriamine based on an at least trihydric alcohol grafted with butylene oxide, with an average molar mass of 400, aliphatic polyetheramine prepared by aminating alcohols grafted with butylene oxide, with an average molar mass of 219, trifunctional, primary polyetheramine prepared by reacting propylene oxide with glycerol, followed by amination of the terminal OH groups, with an average molar mass of 5000, and as hardener component a2) a further amine having a functionality≥2, selected from the group of isophoronediamine, aminoethylpiperazine, 1,3 bis(aminoethyl)cyclohexane, and triethylenetetramine, the ratio of a1) to a2) being in the range from 0.1 to 10:1.

Advantageous is the blend of the invention wherein the mixture comprises as hardener component a1) a polyetheramine selected from the group of polyetheramine D 230, polyetheramine D 400, polyetheramine T 403, polyetheramine T 5000, the hardener component a2) is selected from the group of isophoronediamine, aminoethylpiperazine, 1,3-bis (aminomethyl)cyclohexane, and triethylenetetraamine, and the hardener component b) is tetramethylguanidine, and the ratio of hardener component a1) to hardener component a2) is in the range from 1.5 to 10:1, and 10 to 60 mol % less of mixture is added to the epoxy resin than is needed for the reaction of the active epoxy groups at amine functions of the mixture.

Advantageous is the blend of the invention wherein the blend further comprises fiber-reinforced material.

The invention further provides a process for preparing the blend of the invention, which comprises mixing one or more epoxy resins with the mixture at temperatures below the initial curing temperature of the hardener component a).

Further provided by the invention is the use of the blend of the invention for producing cured epoxy resins.

Advantageous is the inventive use wherein the cured epoxy resins are moldings.

Advantageous is the inventive use wherein the moldings comprise reinforcing material.

The invention further provides a cured epoxy resin obtainable by curing the blend of the invention.

Advantageous is the cured epoxy resin of the invention wherein the cured epoxy resin is a molding.

The invention further provides a molding which is fiber-reinforced.

Advantageous is the molding of the invention obtainable by curing a mold lined with a fiber-reinforced material, and introducing the blend of the invention into the mold by means of infusion technology.

Advantageous is the molding of the invention which constitutes reinforced components for rotor blades of wind turbines.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 1 is a graph showing glass transition temperature as a function of composition.

FIG. 2 is a graph showing flexural strength as a function of composition.

FIG. 3 is a 3D graph showing the relationship between vitrification time, percent TMG, and percent aminic curing.

The blends of the invention comprise at least one and/or two or more epoxy resins and a mixture of a hardener component a) and a hardener component b). The epoxy resins and/or epoxy resin mixtures for use preferably comprise epoxy resins selected from the group of bisphenol A bisglycidyl ether (DGEBA), bisphenol F bisglycidyl ether, bisphenol S bisglycidyl ether (DGEBS), tetraglycidylmethylenedianilines (TGMDA), epoxy novolaks (the reaction products of epichlorohydrin and phenolic resins (novolak)), and cycloaliphatic epoxy resins such as 3,4-epoxycyclohexylmethyl 3,4-epoxycyclohexanecarboxylate and diglycidyl hexahydrophthalate.

Moreover the epoxy resins may also comprise further reactive diluents. These diluents are selected from the group of 1,4-butanediol bisglycidyl ether, 1,6-hexanediol bisglycidyl ether, glycidyl neodecanoate, glycidyl versatate, 2-ethylhexyl glycidyl ether, $C_8$-$C_{10}$ alkyl glycidyl ethers, $C_{12}$-$C_{14}$ alkyl glycidyl ethers, p-tert-butyl glycidyl ether, butyl glycidyl ether, nonylphenyl glycidyl ether, p-tert-butylphenyl glycidyl ether, phenyl glycidyl ether, o-cresyl glycidyl ether, polyoxypropylene glycol diglycidyl ether, trimethylolpropane triglycidyl ether (TMP), glycerol triglycidyl ether, and triglycidyl-para-aminophenol (TGPAP).

In accordance with the prior art a virtually stoichiometric amount is used for the curing of epoxy resins (depending on epoxy resin, 0.9-1.1 equivalents of the hardener/equivalent of epoxy resin). If, however, the mixture of the invention is used for curing epoxy resins, it is preferred to add 10 to 60 mol %, more preferably 20 to 40 mol %, less of the inventive mixture to the epoxy resin than needed for the reaction of the active epoxy groups at amine functions of the mixture. It is particularly preferred if, in total, 0.3 to 0.9 amine equivalent, preferably 0.4 to 0.7 amine equivalent, per epoxide equivalent of the epoxy resin used, of hardener components a1) and a2) is added to the mixture in order to obtain an increase in the pot life and a comparable or improved curing of the epoxy resin as compared with the mixtures of the prior art. For the blend of the invention the fraction of the hardener component a) is 0.3 to 0.9, preferably 0.4 to 0.7, amine equivalent per epoxide equivalent of the epoxy resin used.

For preparing the blend of the invention and for the process of the invention, the mixture is mixed with the epoxy resin at temperatures below the initial curing temperature of the hardener component a). The initial curing temperature is the temperature at which, in a mixture of two or more hardener components having a functionality≥2, the first hardener component reacts with the epoxy resin. This temperature can be determined by a DSC in accordance with DIN 53765 as $T_{RO}^E$.

The hardener component a) in the blend of the invention, and also for the process of the invention, comprises one or more amines having a functionality≥2, at least one amine, when mixed stoichiometrically with the epoxy resin in the 100 g batch, leading at room temperature to a cure time of less than 24 h.

The amines having a functionality≥2 of hardener component a) are all amines known to the skilled worker and having a functionality≥2. Preferably they are selected from the group of 3,6-dioxa-1,8-octanediamine, 4,7,10-trioxa-1,13-tridecanediamine, 4,7-dioxa-1,10-decanediamine, 4,9-dioxa-1,12-dodecanediamine, polyetheramine based on triethylene glycol with an average molar mass of 148, difunctional, primary polyetheramine prepared by aminating an ethylene glycol grafted with propylene oxide, with an average molar mass of 176, difunctional, primary polyetheramine based on propylene oxide with an average molar mass of 4000, difunctional, primary polyetheramine prepared by aminating a polyethylene glycol grafted with propylene oxide, with an average molar mass of 2003, aliphatic polyetheramine based on polyethylene glycol grafted with propylene oxide, with an average molar mass of 900, aliphatic polyetheramine based on polyethylene glycol grafted with propylene oxide, with an average molar mass of 600, difunctional, primary polyetheramine prepared by aminating a diethylene glycol grafted with propylene oxide, with an average molar mass of 220, aliphatic polyetheramine based on a copolymer of poly(tetramethylene ether glycol) and polypropylene glycol with an average molar mass of 1000, aliphatic polyetheramine based on a copolymer of poly(tetramethylene ether glycol) and polypropylene glycol with an average molar mass of 1900, aliphatic polyetheramine based on a copolymer of poly(tetramethylene ether glycol) and polypropylene glycol with an average molar mass of 1400, polyethertriamine based on an at least trihydric alcohol grafted with butylene oxide, with an average molar mass of 400, aliphatic polyetheramine prepared by aminating alcohols grafted with butylene oxide, with an average molar mass of 219, polyetheramine based on pentaerythritol and propylene oxide with an average molar mass of 600, difunctional, primary polyetheramine based on polypropylene glycol with an average molar mass of 2000, difunctional, primary polyetheramine based on polypropylene glycol with an average molar mass of 230, difunctional, primary polyetheramine based on polypropylene glycol with an average molar mass of 400, trifunctional, primary polyetheramine prepared by reacting propylene oxide with trimethylolpropane, followed by amination of the terminal OH groups, with an average molar mass of 403, trifunctional, primary polyetheramine prepared by reacting propylene oxide with glycerol, followed by amination of the terminal OH groups, with an average molar mass of 5000, and a polyetheramine having an average molar mass of 400, prepared by aminating polyTHF which has an average molar mass of 250, 1,12-diaminododecane, 1,10-diaminodecane, 1,2-diaminocyclohexane, 1,2-propanediamine, 1,3-bis(aminomethyl)cyclohexane, 1,3-propanediamine, 1-methyl-2,4-diaminocyclohexane, 2,2'-oxybis(ethylamine), 3,3'-dimethyl-4,4'-diaminodicyclohexylmethane, 4-ethyl-4-methylamino-1-octylamine, diethylenetriamine, ethylenediamine, hexamethylenediamine, isophoronediamine, menthenediamine, xylylenediamine, N-aminoethylpiperazine, neopentanediamine, norbornanediamine, octamethylenediamine, piperazine, 4,8-diaminotricyclo[5.2.1.0]decane, tolylenediamine, triethylenetetramine, and trimethylhexamethylenediamine.

With particular preference the hardener component a) comprises at least two hardener components a1) and a2), with both comprising an amine having a functionality≥2. With very particular preference the hardener component a1) comprises a polyetheramine and the hardener component a2) comprises a further amine having a functionality≥2.

Polyamines with oxygen in their chain are referred to as polyetheramines.

Polyetheramines having a functionality of ≥2 can be used in the blend of the invention and in the process of the invention as hardener component a), and in the mixture of the invention as hardener component a1). They can be prepared inter alia on the basis of alkylene oxides such as ethylene oxide, propylene oxide, butylene oxide or pentylene oxide, polyTHF or 1,4-butanediol and in each case ammonia, and have molar weight distributions. The alkylene oxides used may be the same or different per molecule. The polyetheramines of types D, ED, and EDR are diamines (D type), with ED standing for diamine based on polyethylene glycol (PEG) and EDR standing for reactive diamines based on PEG; the T types are a triol which is grafted with alkylene oxide(s) and which carries an amino group on each of the three termini. XTJ is used for products still intended for trial. The numbers after the letter code, except for the XTJ products, in the name of the polyetheramines gives the average molar mass of the polyetheramine. The polyetheramines used in the mixture of the invention, in the blend of the invention, and in the process of the invention have a functionality of 2.

Typical examples of polyetheramines of hardener component a1) are selected from the group of difunctional, primary polyetheramine based on polypropylene glycol, with an average molar mass of 230, difunctional, primary polyetheramine based on polypropylene glycol, with an average molar mass of 400, difunctional, primary polyetheramine based on polypropylene glycol, with an average molar mass of 2000, difunctional, primary polyetheramines based on propylene oxide, with an average molar mass of 4000, trifunctional, primary polyetheramine prepared by reacting propylene oxide with trimethylolpropane, followed by amination of the terminal OH groups, with an average molar mass of 403, trifunctional, primary polyetheramine prepared by reacting propylene oxide with glycerol, followed by amination of the terminal OH groups, with an average molar mass of 5000. These compounds are also sales products of the companies BASF (Polyetheramines) and Huntsman (Jeffamines) and are available under the following tradenames:

Polyetheramine D 230/Jeffamine® D 230:
comprises polyetheramine based on polypropylene glycol with an average molar mass of 230.

Polyetheramine D 400/Jeffamine® XTJ 582:
comprises difunctional, primary polyetheramine based on polypropylene glycol with an average molar mass of 400.

Polyetheramine D 2000/Jeffamine® D2000/Jeffamine® XTJ 578:
comprises aliphatic, difunctional, primary polyetheramine based on polypropylene glycol with an average molar mass of 2000.

Polyetheramine D 4000:
comprises polyetheramines based on polypropylene glycol with an average molar mass of 4000.

Polyetheramine T 403/Jeffamine® T 403:
comprises polyetheramine prepared by reacting propylene oxide with trimethylolpropane, followed by amination of the terminal OH groups, with an average molar mass of 403.

Polyetheramine T 5000/Jeffamine® T 5000:
comprises polyetheramine prepared by reacting propylene oxide with glycerol, followed by amination of the terminal OH groups, with an average molar mass of 5000.

Jeffamine® ED-600/Jeffamine® XTJ 501:
comprises an aliphatic polyetheramine constructed from a polyethylene glycol grafted with propylene oxide, and having an average molar mass of 600.

Jeffamine® ED-900:
comprises an aliphatic polyetheramine constructed from a polyethylene glycol grafted with propylene oxide, and having an average molar mass of 900.

Jeffamine® ED-2003:
comprises an aliphatic polyetheramine constructed from a polyethylene glycol grafted with propylene oxide, and having an average molar mass of 2000.

Jeffamine® HK-511:
comprises a difunctional, primary polyetheramine prepared by aminating a diethylene glycol grafted with propylene oxide, with an average molar mass of 220.

Jeffamine® XTJ-542:
comprises an aliphatic polyetheramine based on a copolymer of poly(tetramethylene ether glycol) and polypropylene glycol, with an average molar mass of 1000.

Jeffamine® XTJ-548:
comprises an aliphatic polyetheramine based on a copolymer of poly(tetramethylene ether glycol) and polypropylene glycol, with an average molar mass of 1900.

Jeffamine® XTJ-559:
comprises copolymers of poly(tetramethylene ether glycol) and polypropylene glycol with an average molar mass of 1400.

Jeffamine® XTJ-566:
comprises polyethertriamine based on an at least trihydric alcohol grafted with butylene oxide, with an average molar mass of 400.

Jeffamine® XTJ-568:
comprises an aliphatic polyetheramine prepared by aminating alcohols grafted with butylene oxide, with an average molar mass of 219.

Jeffamine® XTJ-616:
comprises a polyetheramine based on pentaerythritol and propylene oxide with an average molar mass of 600.

Jeffamine® EDR-148:
comprises a polyetheramine based on triethylene glycol with an average molar mass of 148.

Jeffamine® EDR-176:
comprises a difunctional, primary polyetheramine prepared by aminating an ethylene glycol grafted with propylene oxide, with an average molar mass of 176.

PoLyTHF-Amine 350:
comprises a polyetheramine prepared by aminating polyTHF with an average molar mass of 250. The resultant polyTHF-amine possesses an average molecular weight of 400.

The polyetheramines of hardener component a1) are preferably selected from the group of difunctional, primary polyetheramine prepared by aminating diethylene glycol, grafted with propylene oxide, with an average molar mass of 220, aliphatic polyetheramine based on polyethylene glycol grafted with propylene oxide, with an average molar mass of 900, aliphatic polyetheramine based on a copolymer of poly(tetramethylene ether glycol) and polypropylene glycol with an average molar mass of 1000, aliphatic polyetheramine based on a copolymer of poly(tetramethylene ether glycol) and polypropylene glycol with an average molar mass of 1900, aliphatic polyetheramine based on a copolymer of poly(tetramethylene ether glycol) and polypropylene glycol with an average molar mass of 1400, polyethertriamine based on an at least trihydric alcohol grafted with butylene oxide, with an average molar mass of 400, aliphatic polyetheramine prepared by aminating alcohols grafted with butylene oxide, with an average molar mass of 219, difunctional, primary polyetheramine based on polypropylene glycol with an average molar mass of 230, difunctional, primary polyetheramine based on polypropylene glycol with an average molar mass of 400, trifunctional, primary polyetheramine prepared by reacting propylene oxide with trimethylolpropane, followed by amination of the terminal OH groups, with an average molar mass of 403, and a polyetheramine based on propylene oxide and glycerol with an average molar mass of 5000. A very particularly preferred polyetheramine is a polyetheramine based on polypropylene glycol with an average molar mass of 230, such as polyetheramine D 230 or Jeffamine® D230, for example.

Hardener components a2) used are further amines having a functionality≥2, selected from the group of 1,12-diaminododecane, 1,10-diaminodecane, 1,2-diaminocyclohexane, 1,2-propanediamine, 1,3-bis(aminomethyl)cyclohexane, 1,3-propanediamine, 1-methyl-2,4-diaminocyclohexane, 2,2'-oxybis(ethylamine), 3,3'-dimethyl-4,4'-diaminodicyclohexylmethane, 4,4'-methylenedianiline, 4-ethyl-4-methylamino-1-octylamine, diethylenetriamine, ethylenediamine, hexamethylenediamine, isophoronediamine, menthenediamine, xylylenediamine, N-aminoethylpiperazine, neopentanediamine, norbornanediamine, octamethylenediamine, piperazine 4,8-diaminotricyclo[5.2.1.0]-decane, tolylenediamine, triethylenetetramine, and trimethylhexamethylenediamine.

In the mixture of the invention, the blend of the invention and also in the process of the invention there may also be accelerants present as well. These are selected from the group of substituted imidazoles such as 1-methylimidazole, 2-methylimidazole, 2-ethyl-4-methylimidazole, 2-phenylimidazole, 1-cyanoethylimidazole, imidazolines such as 2-phenylimidazoline, tertiary amines such as N,N-dimethylbenzylamine, 2,4,6-tris(dimethylaminomethyl) phenol (DMP 30), bisphenol A, bisphenol F, nonyl-phenol, p-tert-butylphenol, phenolic resins of the novolak type, salicylic acid, p-toluene-sulfonic acid, 1,4-diazabicyclo[2.2.2] octane (DABCO), 1,8-diazabicyclo[5.4.0]undec-7-ene (DBU), S-triazine (Lupragen N 600), bis(2-dimethylaminoethyl) ether (Lupragen N 206), pentamethyldiethylenetriamine (Lupragen N 301), trimethylaminoethylethanol-amine (Lupragen N 400), tetramethyl-1,6-hexanediamine (Lupragen N 500), amino-ethylmorpholine, aminopropylmorpholine, aminoethylethyleneurea, ketimines such as Epi-Kure 3502 (a reaction product of ethylenediamine with methyl isobutyl ketone), urons such as 3-(4-chlorophenyl)-1,1-dimethylurea (Monuron), 3-(3,4-dichlorophenyl)-1,1-dimethylurea (Diuron), 3-phenyl-1,1-dimethylurea (Fenuron), and 3-(3-chloro-4-methylphenyl)-1,1-dimethylurea (Chlorotoluron), tolyl-2,4 bis-N,N-dimethylcarbamide (Amicure UR2T), dicyandiamide (DICY), Mannich bases or secondary amines such as dialkylamines, such as di(2-ethylhexyl) amine, dibutylamine, dipropylamine, ditridecyl-amine, N,N'-diisopropylisophoronediamine (Jefflink® XTJ-584), N,N'-diisobutyl-4,4"-diaminodicyclohexylmethane (Clearlink 1000), N-(hydroxyethyl)aniline, and di(2-methoxyethyl) amine, for example.

In addition to the hardener component a) or a1) and a2), the mixture of the invention, the blend of the invention and the process of the invention further comprise a hardener component b) of the formula I

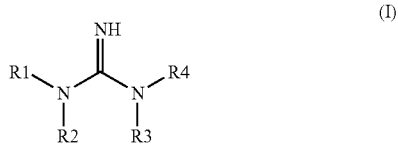

The radicals R1 to R3, R5, and R6 of the formula I in the hardener component b) of the mixture of the invention, of the blend of the invention and also of the process of the invention are each independently selected from the group of an organic radical having 1 to 20 C atoms and hydrogen. Organic radical means all saturated, unsaturated, cyclic or acyclic hydrocarbon radicals which carry no heteroatoms. With particular preference the organic radical has 1 to 10 C atoms.

Organic radicals which are unsaturated and cyclic include aromatic groups. Preferred aromatic hydrocarbon radicals are selected from the group of phenyl, benzyl, xylene, o-tolyl, a phenyl group substituted by one or more $C_2$ to $C_4$ alkyl groups, and benzyl group. Particularly preferred aromatic hydrocarbon radicals are phenyl groups.

The aliphatic hydrocarbon radicals are selected from the group of cyclic and acyclic hydrocarbon radicals. The acyclic aliphatic hydrocarbon radicals are preferred. In this case it is possible with preference, as hydrocarbon radicals, to use those with $C_1$ to $C_{10}$ atoms, more preferably $C_1$ to $C_4$ atoms.

With very particular preference the radicals for R1 to R3, R5, and R6 are selected from the group of methyl, ethyl, n-propyl, isopropyl, n-butyl, sec-butyl, phenyl, and o-tolyl radicals. With very particular preference more particularly, the radicals selected for the radicals R1 to R3, R5 and R6 are the aliphatic hydrocarbon radicals selected from the group of methyl, ethyl, n-propyl, isopropyl, n-butyl or sec-butyl group. With very particular preference more particularly are methyl, ethyl, n-propyl, and n-butyl group.

R4, for the mixture of the invention, the blend of the invention and the process of the invention, is selected, independently of R1 to R3, R5, and R6, from the group of an organic radical having 1 to 20 C atoms and a group —C(NH)NR5R6-. With particular preference R4 is selected from the group of methyl, ethyl, n-propyl, isopropyl, n-butyl, sec-butyl, phenyl and o-tolyl radical. With very particular preference more particularly are methyl, ethyl, n-propyl, n-butyl, and o-tolyl radical.

In one particularly preferred embodiment R1 to R4 independently of one another are organic aliphatic hydrocarbons selected from the group of methyl, ethyl, n-propyl, isopropyl, n-butyl, and sec-butyl radical. With very particular preference more particularly are methyl, ethyl, n-propyl, and n-butyl group.

With very particular preference more particularly the compound of formula I is tetramethylguanidine.

The fraction of the compound of the formula I in the blend of the invention and in the process of the invention is situated in the range from 0.5% to 25% by weight, based on the amount of epoxy resin used.

The fraction of the formula I in the mixture of the invention is situated in the range from 5% to 55%, preferably in the range from 5% to 30%, more preferably between 10% and 25%, by weight, based on the amount of the mixture.

Preferred mixtures of the invention and also blends of the invention are those which in addition to tetramethylguanidine also, additionally, comprise polyetheramines selected from the group of 3,6-dioxa-1,8-octanediamine, 4,7,10-trioxa-1,13-tridecanediamine, 4,7-dioxa-1,10-decanediamine, 4,9-dioxa-1,12-dodecanediamine, difunctional, primary polyetheramine based on polypropylene glycol with an average molar mass of 2000, such as, for example, Jeffamine® D-2000, Jeffamine® XTJ-578 and Polyetheramine D 2000, difunctional, primary polyetheramine based on polypropylene glycol with an average molar mass of 230, such as, for example, Jeffamine® D-230 and Polyetheramine D 230, difunctional, primary polyetheramine based on polypropylene glycol with an average molar mass of 400, such as, for example, Jeffamine® D-400, Jeffamine® XTJ-582 and Polyetheramine D 400, difunctional, primary polyetheramine based on propylene oxide with an average molar mass of 4000, such as, for example, Jeffamine® D-4000, difunctional, primary polyetheramine prepared by aminating a polyethylene glycol grafted with propylene oxide, with an average molar mass of 2003, such as, for example, Jeffamine® ED-2003, aliphatic polyetheramine based on polyethylene glycol grafted with propylene oxide, with an average molar mass of 900, such as, for example, Jeffamine® ED-900, aliphatic polyetheramine based on polyethylene glycol grafted with propylene oxide, with an average molar mass of 2000, such as, for example, Jeffamine® ED-2003, aliphatic polyetheramine based on polyethylene glycol grafted with propylene oxide, with an average molar mass of 600, such as, for example, Jeffamine® ED-600 and Jeffamine® XTJ 501, difunctional, primary polyetheramine prepared by aminating a diethylene glycol grafted with propylene oxide, with an average molar mass of 220, such as, for example, Jeffamine® HK-511, trifunctional, primary polyetheramine prepared by reacting propylene oxide with trimethylolpropane, followed by amination of the terminal OH groups, with an average molar mass of 403, such as, for example, Jeffamine® T-403 and Polyetheramine T 403, trifunctional, primary polyetheramine prepared by reacting propylene oxide with glycerol, followed by amination of the terminal OH groups, with an average molar mass of 5000, such as, for example, Jeffamine® T-5000 and Polyetheramine T 5000, aliphatic polyetheramine based on a copolymer of poly(tetramethylene ether glycol) and polypropylene glycol with an average molar mass of 1000, such as, for example, Jeffamine® XTJ-542, aliphatic polyetheramine based on a copolymer of poly(tetramethylene ether glycol) and polypropylene glycol with an average molar mass of 1900, such as, for example, Jeffamine® XTJ-548, aliphatic polyetheramine based on a copolymer of poly(tetramethylene ether glycol) and polypropylene glycol with an average molar mass of 1400, such as, for example, Jeffamine® XTJ-559, aliphatic polyethertriamine based on an at least trihydric alcohol grafted with butylene oxide, with an average molar mass of 400, such as, for example, Jeffamine® XTJ-566, aliphatic polyetheramine prepared by aminating alcohols grafted with butylene oxide, with an average molar mass of 219, such as, for example, Jeffamine® XTJ-568, polyetheramine based on pentaerythritol and propylene oxide with an average molar mass of 600, such as, for example, Jeffamine® XTJ-616, polyetheramine based on triethylene glycol with an average molar mass of 148, such as, for example, Jeffamine® EDR 148, difunctional, primary polyetheramine prepared by aminating an ethylene glycol grafted with propylene oxide, with an average molar mass of 176, such as, for example, Jeffamine® EDR 176, and a polyetheramine having an average molar mass of 400, prepared by aminating polyTHF with an average molar mass of 250, such as polyTHF Amine 350, for example.

Particularly preferred mixtures of the invention and also blends of the invention are firstly those which besides tetramethylguanidine and polyetheramines selected from the group of difunctional, primary polyetheramine based on polypropylene glycol with an average molar mass of 230, such as, for example, Jeffamine® D-230 and Polyetheramine D 230, difunctional, primary polyetheramine based on polypropylene glycol with an average molar mass of 400, such as, for example, Jeffamine® D-400, Jeffamine® XTJ-582, and Polyetheramine D 400, difunctional, primary polyetheramine prepared by aminating a diethylene glycol grafted with propylene oxide, with an average molar mass of 220, such as, for example, Jeffamine® HK-511, trifunctional, primary polyetheramine prepared by reacting propylene oxide with trimethylolpropane, followed by amination of the terminal OH groups, with an average molar mass of 403, such as, for example, Jeffamine® T-403 and Polyetheramine T 403, aliphatic polyetheramine based on polyethylene glycol grafted with propylene oxide, with an average molar mass of 900, such as, for example, Jeffamine® ED-900, aliphatic polyetheramine based on a copolymer of poly(tetramethylene ether glycol) and polypropylene glycol with an average molar mass of 1000, such as, for example, Jeffamine® XTJ-542, polyetheramine based on a copolymer of poly(tetramethylene ether glycol) and polypropylene glycol with an average molar mass of 1900, such as, for example, Jeffamine® XTJ-548, aliphatic polyetheramine based on a copolymer of poly(tetramethylene ether glycol) and polypropylene glycol with an average molar mass of 1400, such as, for example, Jeffamine® XTJ-559, aliphatic polyethertriamine based on an at least trihydric alcohol grafted with butylene oxide, with an average molar mass of 400, such as, for example, Jeffamine® XTJ-566, aliphatic polyetheramine prepared by aminating alcohols grafted with butylene oxide, with an average molar mass of 219, such as, for example, Jeffamine® XTJ-568, also, additionally, comprise a diamine selected from the group of isophoronediamine, 1,2-diaminocyclohexane, 1-methyl-2,4-diaminocyclohexane, and 1,3-bis(aminomethyl)cyclohexane. A very particularly preferred mixture of the invention is the mixture comprising tetramethylguanidine, difunctional primary polyetheramine based on polypropylene glycol with an average molar mass of 230, such as, for example, Jeffamine® D-230 and Polyetheramine D 230 and isophoronediamine.

In the case of a mixture of the invention and of a preferred blend of the invention in which, in addition to the compound of the formula I, a polyetheramine and a further amine having a functionality≥2 are used, the polyetheramine is present in a ratio with respect to the further amine in the range from 0.1 to 10:1, preferably in the range from 1.5 to 10:1, more preferably in the range from 2.0 to 5.0:1. In an especially preferred mixture of the invention and a more particularly especially preferred blend comprising tetramethylguanidine, Polyetheramine D230/Jeffamine® D230, and isophoronediamine, the preferred mixing ratio of Polyetheramine D230/Jeffamine® D230 to isophoronediamine is in the range from 2.2 to 2.6:1, more preferably in the range from 2.3 to 2.5:1.

The mixture of the invention is mixed from the individual constituents by mechanical methods known to the skilled worker at temperatures below 160° C., preferably in the range from 5 to 30° C.

When the mixture of the invention is utilized to cure epoxy resins, the rate of curing is comparable or better in relation to curing systems from the prior art.

Besides the use of the mixture of the invention in infusion technologies such as, for example, resin infusion, resin transfer molding (RTM), vacuum assisted resin transfer molding (VARTM), which are described in U.S. Pat. No. 3,379,591, the mixtures of the invention and blends of the invention can also be employed for further technologies for the curing of epoxy resins that require a sufficient processing life at temperatures of 15-45° C. in combination with rapid curing at higher temperatures. These technologies are selected from the group of filament winding, pultrusion, hand lay-up and prepreg, as described in U.S. Pat. No. 3,379,591 and U.S. Pat. No. 5,470,517. In the hand lay-up process, a fiber material is wetted manually or mechanically with epoxy resin and then these mats are inserted into a mold and, where two or more layers are used, are consolidated with rollers or similar apparatus. Curing often takes place in a vacuum bag, since this consolidates the material and allows a precise epoxy resin content to be set.

The present invention further provides the cured epoxy resin obtainable by curing the blend of the invention or by curing an epoxy resin or epoxy resin mixture with the mixture of the invention. For this purpose the blends of the invention are either introduced into special molds or applied to surfaces and induced to cure by an increase in temperature. The blends for application to surfaces may further comprise additional fillers in the blends. These fillers are selected from the group of thixotropic agents (hydrophilic and hydrophobic fumed silicas), UV stabilizers (nanoscale oxides such as titanium dioxide and zinc oxide), flame retardants (polyphosphates and phosphorus), silicates, and carbonates for improving the mechanical properties. The molds that are used and into which the blends of the invention are introduced may comprise fiber-reinforcing material or else may comprise elements which are to be protected from environmental effects such as damp, oxygen, dust particles or other aggressive materials or influences.

Preferred cured epoxy resins are those which are cured in a molding. These moldings are selected from the group of moldings for motor vehicles, aircraft, ships, boats, sports goods, and blades for wind turbines. Moldings for rotor blades of wind turbines are particularly preferred.

The moldings may be lined either with or without a fiber-reinforcing material, and/or else fiber-reinforcing materials may additionally be added to the blend of the invention and/or to the mixture of the invention. The fiber-reinforcing materials may therefore be woven fabrics, uniaxial and multiaxial laid fabrics, nonwovens, and short fibers of the following fiber materials: glass fibers, carbon fibers, aramid fibers, PE fibers (Dyneema), and basalt fibers. Preference is given to woven fabrics and to uniaxial and multiaxial lays of glass fibers and carbon fibers. In the case of large components which are fiber-reinforced, the components are preferably lined with the fiber-reinforcing material. Uniaxial and multiaxial lays of glass fibers are particularly preferred. The rotor shells for wind turbines are preferably lined with laid glass fiber fabrics.

The moldings are produced preferably by the process of the invention, in which a corresponding mold is provided, the blend of the invention is introduced into this mold, and the blend is cured to completion only when the mold has been completely filled. In the case of the process of the invention, the blend of the invention, which may comprise the mixture of the invention, is introduced into the corresponding mold preferably by way of the infusion technology. In this case a vacuum is applied to the molding. This vacuum draws the blend comprising epoxy resin and, if desired, the mixture of the invention into the mold under suction at temperatures below the initial curing temperature, and so the viscosity during the filling operation remains virtually unchanged and all of the regions of the molding are filled by the blend before the latter is fully cured. This is followed by complete curing of the blend in the molding. For complete curing it is possible to apply further heat sources from outside.

In the presence of epoxy resins, the mixture of the invention can also be used as a structural adhesive for composite components with one another and also with other materials of construction such as metals and concrete. In this context the mixture of the invention or the blend of the invention can be combined with fibrous fillers such as short glass fibers and with fillers such as thixotropic agents (hydrophilic and hydrophobic fumed silicas), UV stabilizers (nanoscale oxides such as titanium dioxide and zinc oxide), flame retardants (polyphosphates and phosphorus), silicates and carbonates. In relation to the prior art, the structural adhesives combine a long processing life with short curing times under the curing conditions specified above.

EXAMPLES

The state of the art selected was a mixture of Polyetheramine D230 and isophoronediamine in a weight ratio of 70/30.

The blend in which a mixture of Polyetheramine D230 and isophoronediamine and tetramethylguanidine is used comprises 82% by weight of commercial bisphenol A bisglycidyl ether (Epilox A19-03) and 18% by weight of butanediol bisglycidyl ether (Epilox P13-21).

The mixtures of the invention for the curing of the epoxy resin system are composed of mixtures of Polyetheramine D230 and Isophoronediamine (IPDA) at a constant weight ratio of 70/30, to which tetramethylguanidine (TMG) is admixed in varying amounts. The overview of the combinations tested is found in table 1.

TABLE 1

Composition of the combinations investigated

| Test No. Line/Column | Initial mass | | | |
|---|---|---|---|---|
| | Epoxy resin system | Polyetheramine D 230 | IPDA | TMG |
| 1/1 | 38.71 g | 7.90 g | 3.39 g | 0.00 g |
| 1/2 | 38.26 g | 7.81 g | 3.35 g | 0.59 g |
| 1/3 | 37.77 g | 7.71 g | 3.30 g | 1.22 g |
| 1/4 | 37.23 g | 7.60 g | 3.26 g | 1.92 g |
| 1/5 | 36.65 g | 7.48 g | 3.20 g | 2.67 g |
| 1/6 | 35.30 g | 7.20 g | 3.09 g | 4.41 g |
| 2/2 | 39.18 g | 7.20 g | 3.08 g | 0.54 g |
| 2/3 | 38.71 g | 7.11 g | 3.05 g | 1.13 g |
| 2/4 | 38.21 g | 7.02 g | 3.01 g | 1.77 g |
| 2/5 | 37.65 g | 6.91 g | 2.96 g | 2.47 g |
| 2/6 | 36.37 g | 6.68 g | 2.86 g | 4.09 g |
| 3/2 | 40.15 g | 6.55 g | 2.81 g | 0.49 g |
| 3/3 | 39.71 g | 6.48 g | 2.78 g | 1.03 g |
| 3/4 | 39.24 g | 6.41 g | 2.75 g | 1.61 g |
| 3/5 | 38.71 g | 6.32 g | 2.71 g | 2.26 g |
| 3/6 | 37.50 g | 6.12 g | 2.62 g | 3.75 g |
| 4/2 | 41.16 g | 5.88 g | 2.52 g | 0.44 g |
| 4/3 | 40.76 g | 5.82 g | 2.50 g | 0.92 g |
| 4/4 | 40.32 g | 5.76 g | 2.47 g | 1.45 g |
| 4/5 | 39.84 g | 5.69 g | 2.44 g | 2.03 g |
| 4/6 | 38.71 g | 5.53 g | 2.37 g | 3.39 g |
| 5/2 | 42.23 g | 5.17 g | 2.22 g | 0.39 g |
| 5/3 | 41.86 g | 5.13 g | 2.20 g | 0.81 g |
| 5/4 | 41.47 g | 5.08 g | 2.18 g | 1.28 g |
| 5/5 | 41.03 g | 5.02 g | 2.15 g | 1.79 g |
| 5/6 | 40.00 g | 4.90 g | 2.10 g | 3.00 g |
| 6/2 | 43.35 g | 4.42 g | 1.90 g | 0.33 g |
| 6/3 | 43.03 g | 4.39 g | 1.88 g | 0.70 g |
| 6/4 | 42.68 g | 4.35 g | 1.87 g | 1.10 g |
| 6/5 | 42.29 g | 4.32 g | 1.85 g | 1.54 g |
| 6/6 | 41.38 g | 4.22 g | 1.81 g | 2.59 g |
| 7/2 | 44.53 g | 3.64 g | 1.56 g | 0.27 g |
| 7/3 | 44.26 g | 3.61 g | 1.55 g | 0.57 g |
| 7/4 | 43.97 g | 3.59 g | 1.54 g | 0.90 g |
| 7/5 | 43.64 g | 3.56 g | 1.53 g | 1.27 g |
| 7/6 | 42.86 g | 3.50 g | 1.50 g | 2.14 g |
| 8/2 | 45.79 g | 2.80 g | 1.20 g | 0.21 g |
| 8/3 | 45.57 g | 2.79 g | 1.20 g | 0.44 g |
| 8/4 | 45.34 g | 2.78 g | 1.19 g | 0.70 g |
| 8/5 | 45.07 g | 2.76 g | 1.18 g | 0.99 g |
| 8/6 | 44.45 g | 2.72 g | 1.17 g | 1.67 g |
| 9/2 | 47.11 g | 1.92 g | 0.82 g | 0.14 g |
| 9/3 | 46.96 g | 1.92 g | 0.82 g | 0.30 g |
| 9/4 | 46.79 g | 1.91 g | 0.82 g | 0.48 g |
| 9/5 | 46.60 g | 1.90 g | 0.82 g | 0.68 g |
| 9/6 | 46.16 g | 1.88 g | 0.81 g | 1.15 g |
| 10/2 | 48.51 g | 0.99 g | 0.42 g | 0.07 g |
| 10/3 | 48.43 g | 0.99 g | 0.42 g | 0.16 g |
| 10/4 | 48.34 g | 0.99 g | 0.42 g | 0.25 g |
| 10/5 | 48.24 g | 0.98 g | 0.42 g | 0.35 g |
| 10/6 | 48.00 g | 0.98 g | 0.42 g | 0.60 g |

The table below shows the results of the pot life determination by method B at 60° C.

TABLE 2

Determination of pot life by method B at 60° C.
Pot life determination by method B at 60° C.

| | | Parts by weight of TMG in the mixture | | | | | | |
|---|---|---|---|---|---|---|---|---|
| | | 0 | 5 | 10 | 15 | 20 | 30 | Line |
| Percent | 100 | 75 min | 80 min | 85 min | 100 min | 120 min | 125 min | 1 |
| aminic | 90 | | 90 min | 90 min | 100 min | 115 min | 130 min | 2 |
| curing | 80 | | 110 min | 110 min | 145 min | 135 min | 130 min | 3 |
| | 70 | | 150 min | 135 min | 140 min | 140 min | 155 min | 4 |
| | 60 | | 170 min | 160 min | 140 min | 140 min | 135 min | 5 |
| | 50 | | 195 min | 185 min | 165 min | 160 min | 155 min | 6 |
| | 40 | | 270 min | 220 min | 190 min | 175 min | 160 min | 7 |
| | 30 | | — | 285 min | 220 min | 200 min | 180 min | 8 |
| | 20 | | — | — | 290 min | 270 min | 250 min | 9 |
| | 10 | | — | — | — | — | 330 min | 10 |
| Column | | 1 | 2 | 3 | 4 | 5 | 6 | |

For the prior art a pot life (ToB) of 75 min was found.

The tests show (line 1) that the addition of TMG to a mixture of Polyetheramines D230 and IPDA and the use of this blend of the invention leads to an increase in the pot life. A fraction of 30% by weight of TMG in the mixture of the invention or the blend of the invention may raise the pot life by around 66%.

Furthermore, the tests (column 3) show that a reduction in the fraction of the Polyetheramine D230 and of the IPDA (percent aminic curing) in the range from 0.3 to 0.9 amine equivalent per epoxide equivalent results in a more significant increase in the pot life than in the case of the addition of TMG to a stoichiometric mixture of Polyetheramine D230 and IPDA. Thus for a combination of 30% of Polyetheramine D230 and IPDA (aminic curing) and 10% by weight of TMG in the mixture of the invention, an increase in pot life by 380% is achieved.

In addition, the experiments show that the rate of curing between inventive examples and the comparative example is comparable or better. This effect can be demonstrated by determining the vitrification time for a number of selected systems (1/1; 2/4; 3/2; 4/2; 5/3; 6/3; 6.4; 7/4; 8/4; 9/6) (FIG. 3). The vitrification time was determined by means of MDSC as the half-step height of the step-shaped transition of the specific heat capacity. This method is described in the article "Understanding vitrification during cure of epoxy resins using dynamic scanning calorimetry and rheological techniques." (Polymer, 41 (2000) 5949 Ff).

The mixture according to the invention reduces the vitrification time from >6 hours to a time≤3 hours for a curing temperature of 70° C. in comparison to the prior art.

Since the composition of the mixture not only affects the reactivity but also has consequences for other parameters such as glass transition temperature and mechanical characteristics, corresponding investigations were carried out for the systems specified in table 1.

The glass transition temperature (FIG. 1) is depicted as a function of the composition. On the X-axes the fraction of the sum of Polyetheramine D230 and IPDA (aminic curing) (corresponding to lines) is shown, and on the y-axes the weight fraction of the TMG (curing component b)) (corresponding to columns) is shown. The color changes as a function of the glass transition temperature attained. White denotes high glass transition temperature and black denotes low glass transition temperature.

The flexural strength (FIG. 2) is depicted as a function of the composition. Shown on the X-axes is the fraction of the sum of Polyetheramine D230 and IPDA (aminic curing) (corresponding to lines) and on the y-axes the weight fraction of the TMG (hardener component b)) (corresponding to columns) is shown. The color changes as a function of the flexural strength attained. White denotes high and black denotes low flexural strength.

When all of these results are considered, the outcome is that the mixture according to the invention represents an optimum combination of all of the parameters: processing, cure time, and mechanical and thermal properties.

The invention claimed is:

1. A blend comprising
α) one or more epoxy resins and
β) a mixture comprising
a) a hardener component comprising one or more amines having a functionality≥2, wherein at least one of said amines, when mixed stoichiometrically with the epoxy resin in a 100 g batch, leads at room temperature to a cure time of less than 24 h; and
b) a hardener component comprising at least one compound of formula I

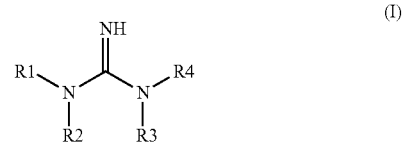

provided in an amount of 5% to 55% by weight, based on the weight of the mixture β) such that the at least one compound of formula I is provided in an amount of 5 to 30% by weight, based on the weight of the mixture β), wherein, R4 is selected from the group consisting of an organic radical having 1 to 20 C atoms and a group —C(NH)NR5R6, R1 to R3, R5 and R6 each independently are an organic radical having 1 to 20 C atoms or hydrogen, and the organic radical having 1 to 20 C atoms for R1 to R6 is a saturated or unsaturated acyclic hydrocarbon radical containing no heteroatoms;
wherein the mixture β) is present in an amount of 10 to 60 mol % less than the amount needed for reaction of the active epoxy groups of the one or more epoxy resins α) and the amine functions of the mixture β), and such that the hardener component a) is present in an amount of 0.4 to 0.9 amine equivalent per epoxide equivalent of the one or more epoxy resins α).

2. The blend according to claim 1, wherein the hardener component a) consists of said one or more amines having a functionality≥2.

3. The blend according to claim 1, wherein the hardener component a) comprises at least two hardener components a1) and a2), the hardener component a1) being at least one polyetheramine having a functionality≥2 and the hardener component a2) being at least one further amine having a functionality≥2.

4. The blend according to claim 3, wherein
the hardener component a1) is selected from the group consisting of 3,6-dioxa-1,8-octanediamine; 4,7,10-trioxa-1,13-tridecanediamine; 4,7-dioxa-1,10-decanediamine; 4,9-dioxa-1,12-dodecanediamine; polyetheramine based on triethylene glycol with an average molar mass of 148; difunctional, primary polyetheramine prepared by aminating an ethylene glycol grafted with propylene oxide, with an average molar mass of 176; difunctional, primary polyetheramine based on propylene oxide with an average molar mass of 4000; difunctional, primary polyetheramine prepared by aminating a polyethylene glycol grafted with propylene oxide, with an average molar mass of 2003; aliphatic polyetheramine based on polyethylene glycol grafted with propylene oxide, with an average molar mass of 900; aliphatic polyetheramine based on polyethylene glycol grafted with propylene oxide, with an average molar mass of 600; difunctional, primary polyetheramine prepared by aminating a diethylene glycol grafted with propylene oxide, with an average molar mass of 220; aliphatic polyetheramine based on a copolymer of poly(tetramethylene ether glycol) and polypropylene glycol with an average molar mass of 1000; aliphatic polyetheramine based on a copolymer of poly(tetramethylene ether glycol) and polypropylene col with an average molar mass of 1900; aliphatic polyetheramine based on a copolymer of poly(tetramethylene ether glycol) and polypropylene glycol with an average molar mass of 1400; polyethertriamine based on an at least trihydric alcohol grafted with butylene oxide, with an average molar mass of 400; aliphatic polyetheramine prepared by aminating alcohols grafted with butylene oxide, with an average molar mass of 219; polyetheramine based on pentaerythritol and propylene oxide with an average molar mass of 600; difunctional, primary polyetheramine based on polypropylene glycol with an average molar mass of 2000; difunctional, primary polyetheramine based on polypropylene glycol with an average molar mass of 230; difunctional, primary polyetheramine based on polypropylene glycol with an average molar mass of 400; trifunctional, primary polyetheramine prepared by reacting propylene oxide with trimethylolpropane, followed by amination of the terminal OH groups, with an average molar mass of 403; trifunctional, primary polyetheramine prepared by reacting propylene oxide with glycerol, followed by amination of the terminal OH groups, with an average molar mass of 5000; and a polyetheramine having an average molar mass of 400, prepared by aminating polyTHF which has an average molar mass of 250; and
the hardener component a2) is selected from the group consisting of 1,12-diaminododecane; 1,10-diaminodecane; 1,2-diaminocyclohexane; 1,2-propanediamine; 1,3-bis(aminomethyl)cyclohexane; 1,3-propanediamine; 1-methyl-2,4-diaminocyclohexane; 2,2'-oxybis(ethylamine); 3,3'-dimethyl-4,4'-diaminodicyclohexylmethane; 4,4'-methylenedianiline; 4-ethyl-4-methylamino-1-octylamine; diethylenetriamine; ethylenediamine; hexamethylenediamine; isophoronediamine; menthenediamine; xylylenediamine; N-aminoethylpiperazine; neopentanediamine; norbornanediamine; octamethylenediamine; piperazine; 4,8-diaminotricyclo[5.2.1.0]decane; tolylenediamine; triethylenetetramine; and trimethylhexamethylenediamine.

5. The blend according to claim 3, wherein the hardener component a1) is selected from the group consisting of: difunctional, primary polyetheramine based on polypropylene glycol, with an average molar mass of 230; difunctional, primary polyetheramine based on polypropylene glycol, with an average molar mass of 400; aliphatic difunctional, primary polyetheramine based on polypropylene glycol, with an average molar mass of 2000; difunctional, primary polyetheramine prepared by aminating a diethylene glycol grafted with propylene oxide, with an average molar mass of 220; trifunctional, primary polyetheramine prepared by reacting propylene oxide with trimethylolpropane, followed by amination of the terminal OH groups, with an average molar mass of 403; aliphatic polyetheramine based on polyethylene glycol grafted with propylene oxide, with an average molar mass of 900; aliphatic polyetheramine based on a copolymer of poly(tetramethylene ether glycol) and polypropylene glycol, with an average molar mass of 1000; aliphatic polyetheramine based on a copolymer of poly(tetramethylene ether glycol) and polypropylene glycol, with an average molar mass of 1900; aliphatic polyetheramine based on a copolymer of poly(tetramethylene ether glycol) and polypropylene glycol, with an average molar mass of 1400; polyethertriamine based on an at least trihydric alcohol grafted with butylene oxide, with an average molar mass of 400; aliphatic polyetheramine prepared by aminating alcohols grafted with butylene oxide, with an average molar mass of 219; trifunctional, primary polyetheramine prepared by reacting propylene oxide with glycerol, followed by amination of the terminal OH groups, with an average molar mass of 5000; and the hardener component a2) is selected from the group consisting of isophoronediamine; aminoethylpiperazine; 1,3 bis(aminoethyl)cyclohexane; and triethylenetetramine; wherein the ratio of a1) to a2) ranges from 0.1 to 10:1.

6. The blend according to claim 3, wherein the hardener component a1) is selected from the group consisting of: difunctional, primary polyetheramine based on polypropylene glycol, with an average molar mass of 230; difunctional, primary polyetheramine based on polypropylene glycol, with an average molar mass of 400; trifunctional, primary polyetheramine prepared by reacting propylene oxide with trimethylolpropane, followed by amination of the terminal OH groups, with an average molar mass of 403; trifunctional, primary polyetheramine prepared by reacting propylene oxide with glycerol, followed by amination of the terminal OH groups, with an average molar mass of 5000; the hardener component a2) is selected from the group consisting of isophoronediamine; aminoethylpiperazine; 1,3-bis(aminomethyl)cyclohexane; and triethylenetetraamine; and the hardener component b) is tetramethylguanidine; wherein the ratio of a1) to a2) ranges from 1.5 to 10:1.

7. The blend according to claim 1, wherein the radicals R1 to R3, R5, and R6 of the compounds of the formula I are each independently selected from the group consisting of hydrogen, methyl, ethyl, n-propyl, isopropyl, n-butyl, and sec-butyl; and R4 is selected from the group consisting of methyl, ethyl, n-propyl, isopropyl, n-butyl, sec-butyl, and a group —C(NH)NR5R6-.

8. The blend according to claim 1, wherein the blend further comprises reinforcing-fiber material.

9. A process for preparing the blend according to claim 1, which comprises mixing one or more epoxy resins α) with the mixture β) at temperatures below the initial curing temperature of the hardener component a).

10. A cured epoxy resin obtained by a process comprising curing the blend according to claim 1.

11. The cured epoxy resin according to claim 10, wherein the cured epoxy resin is a molding.

12. A molding according to claim 11, which is fiber-reinforced.

13. The molding according to claim 12, wherein the molding is a reinforced component for rotor blades of wind turbines.

14. The molding according to claim 12, obtained by a process comprising lining a mold with a reinforcing-fiber material; introducing the blend according to claim 1 into the mold with infusion technology; and curing the blend in the mold.

\* \* \* \* \*